United States Patent [19]
Salamone et al.

[11] Patent Number: 5,618,926
[45] Date of Patent: Apr. 8, 1997

[54] IMMUNOASSAY REAGENTS

[75] Inventors: Salvatore J. Salamone, Rutherford; Stephen Vitone, Upper Montclair, both of N.J.

[73] Assignee: Hoffmann-La Roche Inc., Nutley, N.J.

[21] Appl. No.: 249,676

[22] Filed: May 26, 1994

Related U.S. Application Data

[63] Continuation of Ser. No. 2,519, Jan. 11, 1993, abandoned, which is a continuation of Ser. No. 321,946, Mar. 10, 1989, abandoned.

[51] Int. Cl.$^6$ .................. C07K 17/06; G01N 33/547
[52] U.S. Cl. .................. 530/403; 436/533; 436/815; 436/816; 530/404; 530/405; 530/807; 530/816
[58] Field of Search .................. 530/403, 404, 530/405, 363, 367, 380, 807, 816; 436/533, 815, 86

[56] References Cited

U.S. PATENT DOCUMENTS

| | | | |
|---|---|---|---|
| 3,888,864 | 6/1975 | Cleeland, Jr. et al. | 260/285 |
| 3,917,582 | 11/1975 | Soffer et al. | 260/121 |
| 4,101,549 | 7/1978 | Focella et al. | 344/301 |
| 4,196,185 | 4/1980 | Focella et al. | 424/1 |
| 4,205,952 | 6/1980 | Cais . | |
| 4,223,013 | 9/1980 | Hu et al. | 424/85 |
| 4,262,089 | 4/1981 | Singh et al. | 435/7 |
| 4,275,160 | 6/1981 | Singh et al. | 435/188 |
| 4,318,846 | 3/1982 | Khanna et al. | 260/112 B |
| 4,340,736 | 7/1982 | Focella et al. | 544/361 |
| 4,351,760 | 9/1982 | Khanna et al. | 260/112 R |
| 4,629,691 | 12/1986 | Collins et al. | 435/7 |
| 4,680,338 | 7/1987 | Sundoro | 525/54.1 |

FOREIGN PATENT DOCUMENTS

| | | |
|---|---|---|
| 045334 | 8/1980 | European Pat. Off. . |
| 46004 | 2/1982 | European Pat. Off. . |
| 073611 | 8/1982 | European Pat. Off. . |
| 199042 | 3/1986 | European Pat. Off. . |
| 296883 | 6/1988 | European Pat. Off. . |
| 279308 | 8/1988 | European Pat. Off. . |

OTHER PUBLICATIONS

Erlanger, Methods in Enzymology, 70: 85–104 (1980).
Schwartz et al., J. Org. Chem., 51:5463–5465 (1986).
Earley et al., J. Med. Chem., 11:774–777 (1968).
M. Brinkley, Bioconjugate Chem., vol. 3, pp. 2–13 (1992).

*Primary Examiner*—Mary E. Ceperley
*Attorney, Agent, or Firm*—George W. Johnston; Dennis P. Tramaloni

[57] ABSTRACT

Novel reagents for the detection by immunoassay of drugs in body fluids, their preparation and use are disclosed. The reagents of the present invention correspond to the formula $$P-[A-D]_n$$

where:

D is a drug derivative suitably selective for the determination of the presence of the target drug or drug metabolite, A is an activating linker-spacer group having an N-hydroxysuccinimide or isothiocyanate derived linking moiety, P is a poly(amino acid) or polymer capable of covalently bonding with A, and n is less than 1.

13 Claims, 1 Drawing Sheet

FIG. 1

IMMUNOASSAY REAGENTS

This is a continuation of application Ser. No. 08/002,519, filed Jan. 11, 1993, abandoned, which is a continuation of 07/321,946, filed Mar. 10, 1989, abandoned.

BACKGROUND OF THE INVENTION

This invention relates to the field of the detection of drug use by immunoassay testing of bodily fluids. More particularly the invention relates to the search for reagents which will provide sensitive, specific and reproducible performance in the context of microparticle based immunoassay formats. There is a widely acknowledged need for improvements in such assays for detecting both drugs of abuse and therapeutic agents.

In immunoassay approaches for the detection of drugs, various parent drugs, drug metabolites, as well as synthetic drug derivatives, have been explored as haptenic starting points for the development of one or more reagents in various assay systems. These various compounds have exhibited their own advantages and disadvantages when employed as haptens per se, or when used in, or when further modified for use in, specific immunoassay formats.

The use of such compounds as haptenic ligands in microparticle based immunoassays, i.e., linked to a microparticle substrate in a variety of systems, has also been explored. Usually, these systems have as their goal the enhancement of the speed, specificity and, most importantly, the detection of the ultimate interaction or competition of the microparticle bound ligand with the antibody or drug present in a sample.

SUMMARY OF THE INVENTION

The present invention relates to novel reagents for the detection of drug use by antibody mediated diagnostic testing of a sample of bodily fluid. The reagents of the present invention correspond to the formula:

P—[A—D]$_n$ where:
D is a drug derivative suitably antigenically selective for the determination of the presence of target drug or target drug metabolite,
A is an activating linker-spacer group having an N-hydroxysuccinimide or isothiocyanate derived linking moiety,
P is a poly(amino acid) or polymer capable of covalently bonding with A, and
n is less than 1.

Microparticle reagents fabricated from the foregoing conjugates as well as several of the activated drug derivatives, A—D, constructed for use therein, are further novel aspects of the present invention.

DETAILED DESCRIPTION OF THE INVENTION

The present invention provides new and useful reagents for the detection of drug use in antibody mediated testing of bodily fluids. The reagents of the present invention consist of a poly(amino acid) or polymer conjugate which in turn is useful as an intermediate reagent for binding to microparticular matrix, thereby providing an especially rapid acting, sensitive and accurate reagent for microparticle based testing such as latex agglutination. The reagents of the present invention correspond to the formula:

P—[A—D]$_n$ where:
D is a drug derivative suitably antigenically selective for the determination of the presence of target drug or target drug metabolite,
A is an activating linker-spacer group having an N-hydroxysuccinimide or isothiocyanate derived linking moiety,
P is a poly(amino acid) or polymer capable of covalently bonding with A, and
n is less than 1.

Of particular interest for the use of the subject reagents is the conjugation to an amino group which is part of a poly(amino acid) structure. By poly(amino acid) is intended both polypeptides and proteins whether natural or synthetic. Conjugation of the activated ester to poly(amino acids) or to polymers containing amino groups is carried out by combining the appropriate ratio of the activated ester to poly(amino acid) or amino polymer under mild conditions, normally an organic/buffered aqueous solution of a pH range of about 6 to 9. A typically useful poly(amino acid) for the preparation of the reagents of the present invention is bovine serum albumin (BSA).

The ratio of activated drug derivative A—D to poly(amino acid) or polymer is an essential aspect of the reagents of the present invention and their high degree of sensitivity and reliability for the detection of drugs in the resulting diagnostic test. Because of their excellent antigenic reactivity, it has been found that for the activated drug derivatives of the present invention the ratio n of A—D to P must be less than 1, and typically below 0.5. Thus, allowing for the normally less than 100% yield that can be expected from the conjugation reaction of A—D with P (yields for the activated drug derivatives of the present invention with e.g. bovine serum albumin being most typically in the 50 to 75% range), the starting stoichiometric ratio of A—D to P for the reaction should be selected accordingly.

Figure 1:
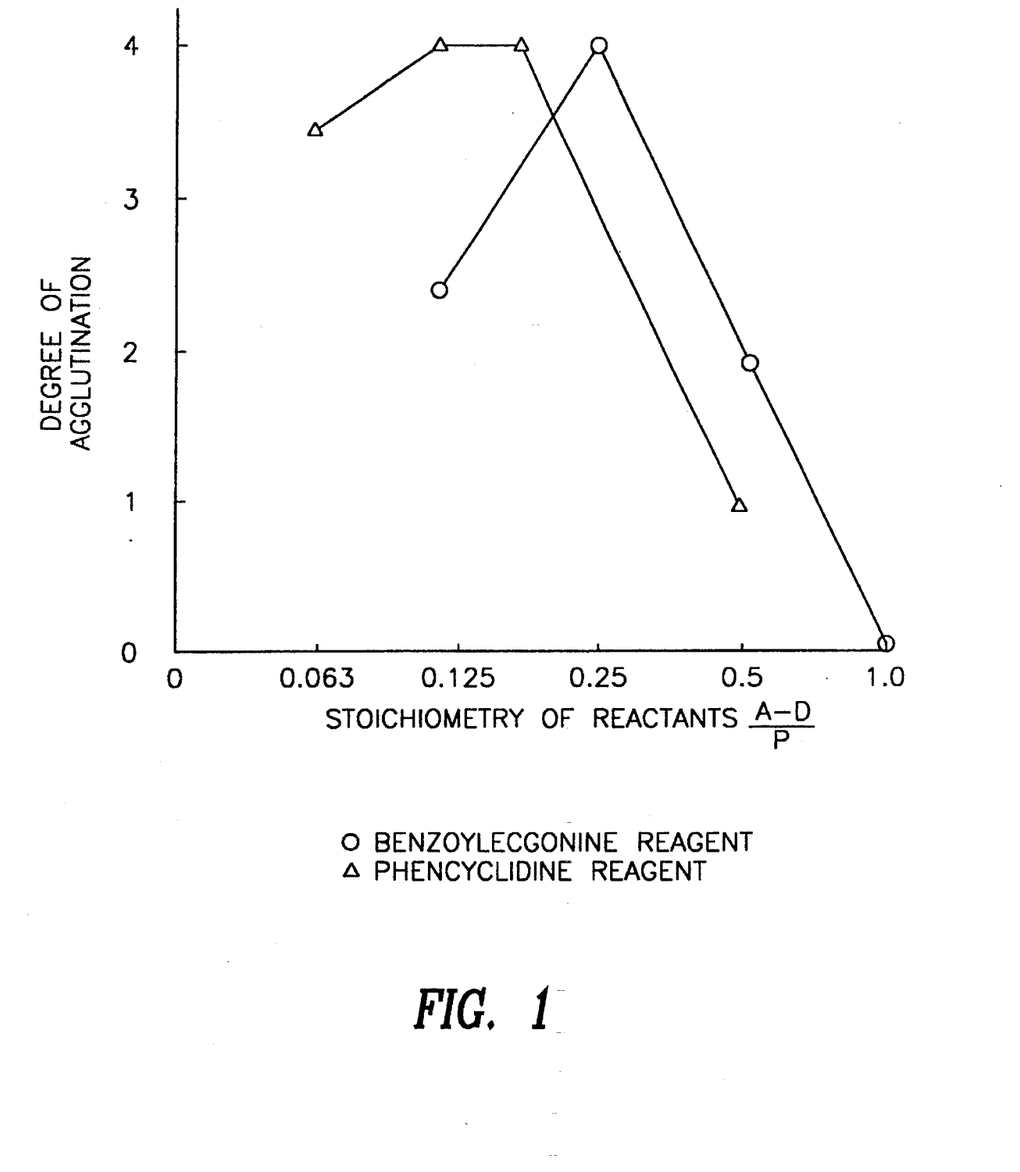
FIG. 1 represents a plotting of the reaction sensitivity against the stoichiometric ratio of the A—D and P reactants used in the preparation of P—[A—D]$_n$ conjugates of the present invention as utilized in a latex microparticle reagent based agglutination assay. Reactivity is plotted as the degree of agglutination on a relative scale of 0 to 4. The graph shows the results of varying ratios for the PCP (phencyclidine) activated derivative N-[1-(4-isothiocyanophenyl)ethyl]-4-[1-(1-piperidinyl)-1-cyclohexyl]benzamide and the benzoylecgonine derivative [1R-(exo,exo,anti)]-8-Methyl-3-[[4-[[[[[[(2,5-dioxopyropyrolidin-1-yl)oxy]carbonyl]phenyl]amino](thioxomethyl)]amino]methyl]benzoyl]oxy]bicyclo[3,2,1]octane-2-carboxylic acid both as the bovine serum albumin-latex microparticle reagent.

The optimal ratio n for a given activated drug derivative in accordance with the present invention can be determined readily by plotting reaction sensitivity in a desired assay format against the stoichiometric ratio of the reactants, i.e., A—D/P. FIG. 1 shows a typical result of such a plotting for PCP (phencyclidine) and cocaine (benzoylecgonine) reagents in the case of a latex agglutination assay format. In accordance with standard practice, these assays are run against minimum clinically effective cutoff concentrations, i.e., as specified by the National Institute on Drug Abuse (Department of Health and Human Services), which for phencyclidine is 25 ng/ml and for cocaine is 300 ng/ml.

The activating linker-spacer group A can be a group of the formula where X is an optional spacing group comprising a benzene, amide, thiourea or urea group or a straight or branched aliphatic chain of $C_{1-10}$, or a combination of the foregoing.

The drug derivative D may be a target drug itself, its metabolite or any other derivative which is sufficiently antigenically selective so as to indicate the presence of target drug or drug metabolite in a tested sample of bodily fluid, e.g., urine.

The activating group A is covalently linked to the drug, drug metabolite or drug derivative of choice at a sterically and reactively appropriate site which in the case of drugs of abuse reagents are preferably as follows:

For amphetamine and methamphetamine: at the ortho, meta or para carbon of the benzene ring, preferably para.

For THC: at the 9 carbon of the $\Delta^8$THC derivatives.

For barbiturate: at the 5 carbon of 5-substituted barbituric acid derivatives.

For phencyclidine: at the ortho, meta or para carbon of the benzene ring, preferably para.

For morphine: at the 3-hydroxyl.

For benzoyl ecgonine: at the meta or para carbon of the benzene ring, preferably para.

For 1,4 benzodiazepines: at the 1 nitrogen.

The reactive amino groups of P bind to A through amide (in the case of N-hydroxysuccinimide ester) or urea or thiourea (in the case of the isothiocyanates) linkage.

The subsequently purified protein conjugate is attached either covalently or hydrophobicly, usually covalently to a microparticle that will be used as the antigenic reagent in a specific diagnostic test for the detection of drug.

Suitable microparticles for the covalent attachment of activated drug derivative-protein conjugates would be carboxylated styrene butadienes, carboxylated polystyrenes, acrylic acid polymers and the like. Suitable micro-particles for the hydrophobic attachment of protein conjugate would be polystyrene, polyvinyltoluene, polydivinylbenzene, polyvinylchloride, polytertiary butylstyrene and the like. Suitable microparticles for the direct covalent attachment of the activated ester would be amino polystyrene, aminopolyvinyltoluene and the like. Suitable magnetic microparticles for the attachment of protein conjugates would be the respective polymer impregnated with a magnetic metal such as ferric or ferrous oxides.

The size of microparticles will typically range from about 0.01 to about 1.0 microns. The size of magnetic microparticles will range from about 0.1 to about 20 microns.

Once the particular microparticle coupled product is formed, it can be utilized in specific diagnostic tests for the detection of drug in biological fluids. It can be used in any convenient concentration, depending upon the specific test, the mode of reading the results and the type of samples involved. In a urine latex assay visualized by the naked eye the concentration by weight, of latex solids will be from about 0.1 to about 5.0%. In a urine latex assay employing an instrument to determine the degree of turbidity, in the range of 340 to 720 nanometers, the concentration by weight of latex solids will be from about 0.001 to about 1.0% A typical visual latex test is described in U.S. Pat. No. 4,101,549.

For barbiturate, a preferred activated drug derivative is the N-hydroxysuccinimide ester derivative of the formula:

The above derivative, along with other useful derivatives in accordance with the present invention, may be prepared by reacting the appropriate barbituric acid derivative such as disclosed in U.S. Pat. No. 4,101,549, with N-hydroxysuccinimide in the presence of a carbodiimide. The preferred conjugate reagent may in turn be formed by binding the activated drug derivative to a poly(amino acid) or polymer generally through an amide linkage.

For morphine, preferred activated drug derivatives are the isothiocayanato derivatives of the formula:

where $R_1$ is hydrogen, methyl or acetyl, preferably hydrogen; a is 2 to 8, and is preferably 3; and the isothiocyanate moiety is in the meta or para position.

These isothiocyanates may be prepared by reacting the appropriately protected aminobenzoic acid with the desired alkylamino opiate derivative, such as disclosed in U.S. Pat. No. 3,888,864. The amino group is then deprotected and derivatized to the isothiocyanate using thiophosgene under mild conditions. The conjugated reagents are in turn formed by binding the activated drug derivative to a poly(amino acid) or polymer generally through a thiourea linkage.

For amphetamine and methamphetamine*, a preferred activated drug derivative is the N-hydroxysuccinimide ester derivative of the formula:

where: $R^2$ is hydrogen in the case of amphetamine and methyl in the case of methamphetamine, b is 1 to 9, preferably 3, and the alkyl chain is meta or para, preferably para.

* Unless otherwise specified, references herein to drugs or drug derivatives having known optical isomeric forms is to be taken as referring inclusively to the optical antipodes or racemate.

The activated ester is prepared by reacting d-amphetamine (or methamphetamine) with trifluoroacetic anhydride. The resulting N-protected amphetamine is reacted with succinic anhydride in the presence of aluminum chloride to give a substituted protected amphetamine which contains an acid and ketone. The ketone is reduced with palladium on charcoal in an atmosphere of hydrogen and the acid is then converted to an activated ester with N-hydroxysuccinimide in the presence of a carbodiimide.

The protecting group, in this case the trifluoroacetyl, is removed prior to use in an antibody mediated assay, as for example after preparing a microparticle (e.g. latex) reagent.

For tetrahydrocannabinoid, a preferred activated drug derivative is the N-hydroxysuccinimide ester derivative of the formula:

Such derivatives may be prepared by reacting the appropriate cannabinoid derivative, such as disclosed in *J. Org. Chem.* (1986), 51, pp. 5463–5465 with N-hydroxysuccinimide in the presence of a carbodiimide.

For phencyclidine (PCP), preferred activated drug derivatives are the isothiocyanate of the formula as well as the N-hydroxy succinimide ester derivative of the formula

The PCP isothiocyanate derivative may be prepared by reacting the PCP acid as disclosed in U.S. Pat. No. 4,196,185, with thionyl chloride followed by reaction with R-(+)p-nitro-α-methylbenzylamine hydrochloride. The nitro group is reduced with Raney nickel (H₂, ethanol) and the resulting amino group is converted to an isothiocyanate in the same manner as described in Example 1 of this patent.

The PCP N-hydroxysuccinimide ester derivative may be prepared by reacting the PCP acid as disclosed in U.S. Pat. No. 4,196,185 in the same manner as described in Example 7 of this patent.

For benzoyl ecgonine, the preferred activated drug derivative is the N-hydroxysuccinimide ester derivative of the formula:

where $R^3$ is hydrogen or methyl, preferably hydrogen.

These ester derivatives may be prepared by reacting methylecgonine with the acid chloride of para-cyanobenzoic acid. The nitrile is reduced with Raney nickel (55 psi H₂, methanol) and the methyl ester is then removed in boiling water. The amino group is then reacted with the isothiocyanate of para-aminobenzoic acid and the activated ester is prepared in the same manner as described in Example 7 of this patent.

For benzodiazepines, a preferred activated drug derivative is the isothiocyanate derivative of the formula:

This isothiocyanate may be prepared by reacting 1-(2-aminoethyl)-7-chloro-1,3-dihydro-5-(2-fluorophenyl)-2H-1,4-benzodiazepin-2-one as disclosed in *J. Med. Chem.*, (1968), 11, pp. 774–777 in the same manner as described in Example 1 of this patent where the amino group is reacted with protected para-aminobenzoic acid and carried on to the isothiocyanate.

Of the foregoing activated drug derivatives, the following compounds are most preferred:

For morphine: N-[3-[7,8-Didehydro-4,5-epoxy-6-hydroxy-17-methylmorphinan-3-yl)oxy]propoxy]-4-isothiocyanatobenzamide.

For barbiturate: 5-[3-[2,5-Dioxo-1-pyrrolidinyl)oxy]-1-methyl-3-oxo=propyl]-5-(2-propenyl)2,4,6(1H,3H,5H)pyrimidinetrione.

For amphetamine: (S)-N[2-[4-[4-[(2,5-Dioxo-1-pyrrolidinyl-oxy]-4-oxo-butyl]phenyl]-1-methyl-ethyl]-2-trifluoacetamide.

For methamphetamine: (S)-N-Methyl-N[2-[4-[4-[(2,5-dioxo-1-pyrrolidinyl)-oxy]-4-oxo-butyl]phenyl]-1-methyl-ethyl]-2-trifluoroacetamide.

For tetrahydrocannabinoids: 1-[[(6a,7,10,10a-Tetrahydro-1-hydroxy-6,6-dimethyl-3-pentyl-6H-dibenzo)oxy][b,d]pyran-1-yl(carbonyl)oxy]-2,5-pyrrolidinedione.

For phencyclidine: N-[1-(4-Isothiocyanophenyl)ethyl]-4-[1-(1-piperidinyl)-1-cyclohexyl]benzamide.

For benzodiazepines: N-[2-[7-Chloro-5-(2-fluorophenyl)-2,3-dihydro-2-oxo-1H-1,4-benzodiazepin-1-yl]ethyl]-4-isothiocyanatobenzamide.

For benzoylecgonine: [1R-(exo,exo,anti)]-8-Methyl-3-[[4-[[[[[[(2,5-dioxopyrolidin-1-yl)oxy]carbonyl]phenyl]amino](thioxomethyl)]amino]methyl]benzoyl]oxy]bicyclo[3,2,1]octane-2-carboxylic acid.

Preferred poly(amino acid) conjugates of the above activated drug derivatives are the bovine serum albumin (BSA) conjugates and the preferred microparticle reagent embodiment incorporates these conjugates by covalent amide bonding to the surface of carboxylated latex microparticles.

The invention is further explained and illustrated in the following examples. All temperatures are in degrees centigrade.

EXAMPLE 1

Preparation of opiate reagent

Preparation of N-[3-[(7,8-Didehydro-4,5-epoxy-6-hydroxy-17-methylmorphinan-3-yl)oxy]propoxy]-4-N-(butylcarbamoyl)benzamide.

A stirred solution of 0.5 g (1.46 mmol) of 3-0-aminopropylmorphine and 0.5 g (2.1 mmol) of p-(1-t-butoxyformamido)benzoic acid (formed by treating p-Aminobenzoic acid with di-t-butyldicarbonate in the presence of 1N NaOH) in 20 ml of methylene chloride and 5 ml of dry dimethyl formamide was treated with 0.5 g (2.6 mmol) of 1-(3-dimethylaminopropyl)-3-ethylcarbodiimide hydrochloride and stirred at room temperature overnight. The reaction mixture was washed with water (3×25 ml), dried over anhydrous sodium sulfate and concentrated in vacuo. The residue was chromatographed on 100 g of silica using 15% methanol-chloroform as eluent to give 0.77 g (1.37 mmol) of N-[3-[(7,8-Didehydro-4,5-epoxy-6-hydroxy-17-methylmorphinan-3-yl)oxy]propoxy]-4-(N-t-butyl-carbamoyl)-benzamide NMR (CDCl$_3$)δ1.64 (s,9H,t-butyl), 2.56(s,3H,N—CH$_3$), 4.98(d,J=6 Hz, 1H, ArOCH), 7.52(d,J=9H$_2$, 2 Hz, Ar), 7.88(d,J=9 Hz, 2H, Ar).

Preparation of N-[3-[(7,8-Didehydro-4,5-epoxy-6-hydroxy-17-methylmorphinan-3-yl)oxy]propoxy]-4-aminobenzamide:

A stirred solution of 0.7 g (1.24 mmol) of N-[3-[(7,8-Didehydro-4,5-epoxy-6-hydroxy-17-methylmorphinan-3-yl)oxy]propoxy]-4-N-(butylcarbamoyl)benzamide in 25 ml of methylene chloride was treated with 5 ml of trifluoroacetic acid and stirred at room temperature for 30 min. The solvent was removed in vacuo and the residue was dissolved in methylene chloride, washed with saturated aqueous sodium bicarbonate, dried over anhydrous sodium sulfate, and concentrated in vacuo to give 0.5 g of N-[3-[(7,8-Didehydro-4,5-epoxy-6-hydroxy-17-methylmorphinan-3-yl)oxy]propoxy]-4-aminobenzamide.

NMR(CDCl$_3$) δ2.53(s,3H,N—CH$_3$), 4.85 (d,J=6 Hz, 1H, ArOCH), 5.22 (d,J=10 Hz, 1H, vinyl), 5.69 (d,J=10 Hz, 1H, vinyl), 6.45–6.66 (m, 4H, Ar), 7.61 (d,J=8 Hz, 2H, Ar).

Preparation of N-[3-[(7,8-Didehydro-4,5-epoxy-6-hydroxy-17-methylmorphinan-3-y1)oxy]propoxy]-4-isothiocyanatobenzamide:

A stirred solution of 0.5 g (1.1 mmol) of N-[3-[(7,8-Didehydro-4,5-epoxy-6-hydroxy-17-methylmorphinan-3-yl)oxy]propoxy]-4-aminobenzamide in 10 ml of methylene chloride was treated with 0.5 g of solid anhydrous sodium bicarbonate followed by 150 ul (1.9 mmol) of thiophosgene and stirred at room temperature for 30 minutes. The solvent was removed in vacuo and the residue was chromatographed on 150 g of silica gel using 15% methanol-chloroform to give 230 mg of N-[3-[(7,8-Didehydro-4,5-epoxy-6-hydroxy-17-methylmorphinan-3-yl)oxy]propoxy]-4-isothiocyanatobenzamide as an amorphous solid.

IR(CHCl$_3$) 3435(NH), 2100(NCS), 1652 (Amido),NMR(CDCl$_3$-DMSO-d6) δ1.92(s,1,CH of CH$_2$), 2.07(t,J=6 Hz, 2H,CH$_2$), 3.08(d,J=19 Hz,1,CH of CH$_{c2}$), 3.53(bs,1,OH), 4.88(d,J=6 Hz, 1H,ArOCH), 5.28(d,J=10 Hz,1H, vinyl), 5.72(d,J=10 Hz, 1H, vinyl), 6.57 (d,J=6 Hz, 2H, Ar), 6.69 (d,J=6 Hz, 2H, Ar), 7.28(d,J=9 Hz, 2H, At), 7.91(d,J=9 Hz, 2H, Ar), 7.55(bs,1H,NH). MS,(+FAB) m/e 504(M+H)

Conjugation of N-[3-[7,8-Didehydro-4,5-epoxy-6-hydroxy-17-methylmorphinan-3 -yl)oxy]propoxy]-4-isothiocyanatobenzamide (opiate) to Bovine Serum Albumin (BSA)

To a solution (175 mL) containing sodium bicarbonate (0.05M), 10% dimethylsulfoxide (DMSO), and BSA (5.0 g) at pH 8.0, 25° the isothiocyanate (0.004 g in 14 mL of DMSO) was added dropwise. The reaction was stirred at 4° for 15 h at which point it was transferred to dialysis tubing and dialyzed first into an aqueous sodium bicarbonate DMSO (10%) solution (0.05M, pH 8, 4×10 volumes) and then into a sodium bicarbonate buffer (0.05M, pH 8, 7×10 volumes). After dialysis the protein concentration was measured and adjusted to 0.005 g per mL.

EXAMPLE 2

Preparation of sensitized latex containing the opiate-BSA conjugate—general procedure.

To a stirred latex (Seradyn carboxy modified polystyrene 0.888 microns) suspension (180 mL, 10% solids), N-hydroxybenzotriazole (NHB) (0.6 g in 24 mL of aqueous dimethylformamide) and 1-cyclohexyl-3-(2-morpholinoethyl)-carbodiimide metho p-toluenesulfonate (CMC) (2.0 g in 32 mL of water) were added. The suspension was stirred for 3 h at 4° then diluted to 2% latex and extensively washed with water by tangential flow filtration. To the washed 2% latex were added 900 mL of the opiate-BSA solution from Example 1. The reaction was stirred overnight at 4° and was again extensively washed with water by tangential flow filtration. The washed latex was then adjusted to a 3% latex solids (by weight) concentration.

EXAMPLE 3

Opiate Test

Preparation of reaction buffer for test:

This diluent consists of the following aqueous solution at pH 7.5:

1. Pipes [0.20M, 1,4-piperazine bis(ethanesulfonic acid)]
2. PVP [0.50%, Polyvinylpolypyrrolidone]
3. PEG 8000 [1.50%, Poly(ethylene glycol)]
4. Sodium Chloride [10%]
5. Sodium Azide [0.1%]

Preparation of antiserum buffer for test:

Purified mouse monoclonal antibody against opiates is diluted in an appropriate buffer system. This diluent consists of the following in aqueous solution in pH 7.0:
1. Pipes (0.05M)
2. BSA (0.25%)
3. Sodium Chloride (0.15%)
4. Sodium Azide (0.15%)

Test Methodology:

Ten microliters of opiate free urine is dispensed into a mixing well of a capillary agglutinography slide followed by 50 microliters each of antiserum buffer, reaction buffer and latex (example 2). The added liquids are stirred for three seconds and the solution is moved to allow contact with the capillary. The liquid will move through the capillary and fill the viewing area at the end of the capillary in three to six minutes. The liquid in the viewing area will appear as fine floccules (agglutinated) or milky. For negative samples agglutination should be very strong with very little cloudiness.

The dilution of a particular antiserum which is chosen for the test is the one which has the highest dilution that will still produce strong agglutination in the viewing area. When various amounts of opiates are dissolved in opiate free urine in the test systems, no agglutination occurs. The amount of opiate required to inhibit the agglutination will vary from 100 nanograms per mL or greater depending on the concentration of antiserum used and the strength of antiserum produced. Thus, for the system described above a urine containing 300 nanograms of opiate per mL is sufficient to partially inhibit agglutination and a urine containing 600 nanograms of opiate per mL is sufficient to completely inhibit agglutination.

The following table reports the type of cross-reactivity that is observed in the system described above:

|  | Concentration (ng/mL) equivalent to 300 ng/mL of Morphine | % Cross reactivity |
| --- | --- | --- |
| Codeine | 250 | 120 |
| Dihydrocodeine bitartrate | 500 | 60 |
| Dihydromorphine | 400 | 75 |
| Ethylmorphine HCl | 400 | 75 |
| Hydrocodone bitartrate | 800 | 38 |
| Hydromorphone HCl | 800 | 38 |
| Meperidine | 50,000 | <0.6 |
| Morphine 3-glucuronide | 800 | 38 |
| N-Norcodeine HCl | 100,000 | <0.3 |
| Oxycodone | 50,000 | <0.6 |
| Thebaine | 1,600 | 19 |

The following table reports the type of specificity and accuracy that is observed with the above described assay when used with samples positive for opiates:

|  |  | Gas Chromatography- Mass Spectroscopy |  |
| --- | --- | --- | --- |
|  |  | + | − |
| Agglutination Test | + | 54 | |
|  | − | | 0 |

EXAMPLE 4

Preparation of barbiturate reagent

Preparation of 5-[3-[(2,5-Dioxo-1-pyrrolidinyl)oxy]-1-methyl-3-oxopropyl]-5-(2-propenyl)-2,4,6(1H,3H,5H)pyrimidinetrione:

To a solution of 5-allyl-5-(1-carboxyisopropyl)barbituric acid (5 g, 19.6 mmol) in methylene chloride (150 mL) and dimethylforamide (25 mL), N-hydroxysuccinimide (2.5 g, 21.7 mmol) and 1-(3-dimethylaminopropyl)-3-ethylcarbodiimide hydrochloride (4.5 g, 23.4 mmol) were added. The reaction was stirred overnight at room temperature and was then concentrated in vacuo. The residue was dissolved in methylene chloride washed three times with hydrochloric acid (0.2N, 200 mL), once with water and once with sodium bicarbonate. During the washings, a precipitate formed which was filtered to yield 2.4 grams of product. The aqueous phase was extracted with ethylacetate and all organic layers were combined, dried ($Na_2SO_4$), filtered and solvents evaporated to yield an additional 1.0 g of product.

IR(KBr), 3245(Broad NH), 1810–1685(C=O) $cm^{-1}$, $^1$H NMR(DMSO-$d_6$), δ0.97(d,J=6 Hz, 3H, $CH_3$), 2.55–2.78(m, 4H, $CH_2$), 2.82 (s, 4H, $CH_2$), 5.11(t, 2H, $CH_2$, Vinyl), 5.52(m, 1H, CH, Vinyl), 11.68(bs, 2H, NH) MS, (+)FAB, m/e 352(M+H)

Anal. Calc. for C, 51.28; H, 4.87; N, 11.96; Anal. found for C, 51.06; H, 4.91; N, 11.94.

Conjugation of 5-[3-[(2,5-Dioxo-1-pyrrolidinyl)oxy]-1-methyl-3-oxopropyl]-5-(2-propenyl)-2,4,6 (1H, 3H, 5H)pyrimidine-trione (barbiturate) to Bovine Serum Albumin (BSA)

To a solution (400 mL) containing sodium bicarbonate (0.05M), 10% dimethylsulfoxide (DMSO), and BSA (6.0 g) at pH 8.5, 25° the N-hydroxysuccinimide ester (0.008 g in 6.6 mL of DMSO) was added dropwise. The reaction was stirred at 4° for 15 h at which point it was transferred to dialysis tubing and dialyzed first into an aqueous sodium bicarbonate-DMSO (10%) solution (0.05M, pH 8, 4×10 volumes) and then into a sodium phosphate buffer (0.05M, pH 7, 7×10 volumes). After dialysis the protein concentration was measured and adjusted to 0.005 g per mL.

EXAMPLE 5

Preparation of sensitized latex containing the barbiturate-BSA conjugate general procedure.

To a stirred latex (Seradyn carboxy modified polystyrene 0.888 microns) suspension (180 mL, 10% solids), N-hydroxybenzotriazole (NHB) (0.6 g in 24 mL of aqueous dimethylformamide) and 1-cyclohexyl-3-(2-morpholinoethyl)carbodiimide metho p-toluenesulfonate (CMC) (2.0 g in 32 mL of water) were added. The suspension was stirred for 3 h at 4° then diluted to 2% latex and extensively washed with water by tangential flow filtration. To the washed 2% latex were added 900 mL of the barbiturate-BSA solution from Example 4. The reaction was stirred overnight at 4° and was again extensively washed with water by tangential flow filtration. The washed latex was then adjusted to a 3% latex solids (by weight) concentration.

EXAMPLE 6

Barbiturate Test

Preparation of reaction buffer for test:

This diluent consists of the following in aqueous solution at pH 7.5:
1. Hepes [0.20M, 4-(2-hydroxyethyl)-1-piperazineethane-sulfonic acid]
2. PVP [0.50%, Polyvinylpolypyrrolidone]
3. PEG 8000 [1.00%, Poly(ethylene glycol)]
4. Sodium Chloride [1.5%]

5. Sodium Azide [0.1%]

Preparation of antiserum for test:

Rabbit antiserum against barbiturates is diluted in an appropriate buffer system. This diluent consists of the following in aqueous solution at pH 8.0:

1. Hepes, (0.05M)
2. BSA (0.25%)
3. Sodium Chloride (0.15%)
4. Sodium Azide (0.15%)

Test Methodology:

Ten microliters of barbiturate free urine is dispensed into a mixing well of a capillary agglutinography slide followed by 50 microliters each of antiserum buffer, reaction buffer and latex (example 5). The added liquids are stirred for three seconds and the solution is moved to allow contact with the capillary. The liquid will move through the capillary and fill the viewing area at the end of the capillary in three to six minutes. The liquid in the viewing area will appear as fine floccules (agglutinated) or milky. For negative samples agglutination should be very strong with very little cloudiness.

The dilution of a particular antiserum which is chosen for the test is the one which has the highest dilution that will still produce strong agglutination in the viewing area. When various amounts of barbiturates are dissolved in barbiturate free urine in the test systems, no agglutination occurs. The amount of barbiturate required to inhibit the agglutination will vary from 100 nanograms per mL or greater depending on the concentration of antiserum used and the strength of antiserum produced. Thus, for the system described above a urine containing 200 nanograms of barbiturate per mL is sufficient to partially inhibit agglutination and a urine containing 400 nanograms of barbiturate per mL is sufficient to completely inhibit agglutination.

The following table reports the type of cross-reactivity that is observed in the system described above:

|  | Concentration (ng/mL) equivalents to 200 ng/mL of secobarbital | % Cross-reactivity |
| --- | --- | --- |
| Allobarbital | 200 | 100 |
| Allylcyclopentylbarbituric acid | 25 | 800 |
| Amobarbital | 200 | 100 |
| Aprobarbital | 200 | 100 |
| Barbital | 100 | 200 |
| Butabarbital | 250 | 80 |
| p-Hydroxyphenobarbital | 700 | 29 |
| Methobarbital | 25,000 | 0.9 |
| Pentobarbital | 500 | 40 |
| Phenobarbital | 700 | 29 |

The following table reports the type of specificity and accuracy that is observed with the above described assay when used with samples positive for barbiturates:

|  |  | Gas Chromatography- Mass Spectroscopy | |
| --- | --- | --- | --- |
|  |  | + | − |
| Agglutination Test | + | 48 | |
|  | − | 0 | |

EXAMPLE 7

Preparation of amphetamine reagent

Preparation of (S)-N-(1-methyl-2-phenylethyl) fluoroacetamide(1):

To a mixture of d-amphetamine sulfate (20.0 g, 0.108 mol) in triethylamine (75 mL) that was purged with argon and cooled in an ice bath trifluoroacetic anhydride (31 mL) was added dropwise over 15 min. The reaction was stirred at ambient temperature overnight. The solvents were then evaporated in vacuo and the residue was dissolved in methylene chloride (200 mL), washed with 5% aqueous tartaric acid (3×250 mL), dried ($Na_2SO_4$), filtered and concentrated in vacuo to yield a yellow oil. The material was crystallized in a hexane ether mixture to yield 14 g of the product.

$^1$H NMR ($CDCl_3$) δ1.17 (d J=6 Hz, 3H, $CH_3$), 2.78 (t, J=5 Hz, 2H, $CH_2$), 4.22 (m, J=6 Hz, 1H, CH), 6.00 (bs, 1H, NH), 7.06 (d, J=6 Hz, 2H, Ar), 7.22 (m, 3H, Ar)

Preparation of (S)-4-[2-methyl-2-[(trifluoroacetyl)amino]-ethyl]-p-oxo-benzenebutanoic acid (2):

To a stirred solution of (1), (12.0 g, 0.05 mol) in methylene chloride (210 mL) under argon, succinic anhydride (8.0 g, 0.08 mol) was added. The reaction was cooled in an ice bath and then treated with aluminum chloride (28.0 g, 0.21 mol), portionwise over 5 min. The reaction was stirred at 0°–5° for 2 h and then at room temperature overnight. Hydrochloric acid (3N, 120 mL) was then slowly added and then solution was stirred for an additional one hour. The methylene chloride was removed in vacuo and the aqueous layer was extracted with ethyl acetate. The organic layer was dried ($Na_2SO_4$), filtered and the solvents evaporated to yield a tan residue which upon trituration with ether gave 10.5 g of product.

IR($CHCl_3$) 3300(NH), 1700 (Acid+Amide), 1555 (Amide) $cm^{-1}$, $^1$H NMR($CDCl_3$+DMSO-$d_6$) δ1.21(d,J=7 Hz, 3H, $CH_3$), 2.73 (t, J=6 Hz, 2H, $CH_2$), 2.82(m, 1H, H of $CH_2$), 2.95(m, 1H, H of $CH_2$), 3.27 (t, J=6 Hz, 2H, $CH_2$), 4.25(1H, CH), 7.27(d, J=8 Hz, 2H, Ar), 7.92(d, J=8 Hz, 2H, Ar), 7.57(bs, 1H, NH). Ms, m/e 331(M+)

Preparation of (S)-4-[2-methyl-2-[trifluoroacetyl)amino]-ethyl]benzenebutanoic acid (3):

A mixture of 2 (9.2 g, 0,027 mol), and 10% palladium on charcoal (4.0 g) in acetic acid (400 mL) was hydrogenated at 50 psi for 24 h. The catalyst was filtered off, the filtrate was concentrated in vacuo and the residue was triturated with ether to yield 7.0 g of a white product.

IR($CHCl_3$) 3425(NH), 1718(Acid), 1532(Amide), 1170($CF_3$) $cm_{-1}$, $^1$H NMR($CDCl_3$) δ1.16(d, J=7 Hz , 3H, CH3), 1.92(m, 2H, $CH_2$), 2.34(bs, 2H, AR—$CH_2$), 2.63 (m, 2H, $CH_2$), 2.79(m,2H,$CH_2$), 4.28(m, 1H, CH), 5.94(bs, 1H, NH), 6.97(d, J=8 Hz, 2H, AR), 7.03(d, J=8 Hz, 2H, AR). MS, m/e 299(M—$H_2O$)

Preparation of (S)-N-[2-[4-[4-[(2,5-Dioxo-1-pyrrolidinyl)-oxy]-4-oxo=butyl]phenyl]-1-methyl-ethyl]-2-trifluoroacetamide (4)

To a stirred solution of 3 (5.4 g, 0.019 mol) in methylene chloride (150 mL), tetrahydrofuzan (150 mL) and dimethylforamide (50 mL), N-hydroxysuccinimide (2.7 g, 0.023 mol) and 1-(3-dimethylaminopropyl)-3-ethyl carbodiimide hydrochloride (6.0 g, 0.031 mol) was added. The reaction was stirred at room temperature overnight, and then was concentrated in vacuo. The resulting residue was dissolved in methylene chloride, filtered and purified by silica gel chromatography (7% ether-methylene chloride as eluent) to give a yellow oil which crystallized in a ether to yield 3.7 g of a white product.

IR($CHCl_3$), 3425(NH), 1812–1741(Imide), 1725(Amide), 1170($CF_3$) $cm^{-1}$. $^1$H NMR($CDCl_3$) δ1.21(d J=7 Hz 3H $CH_3$), 2.07(m, 2H, $CH_2$), 2.60(t, J=7 Hz, 2H, $CH_2$), 2.72 (t, J=7 Hz, 2H, CH$_2$), 2.80–2.90(m, 6H, CH$_2$), 4.27(m, 1H, CH), 6.10(bs, 1H, NH), 7.09(d, J=8 Hz, 2H, Ar), 7.15(d, J=8 Hz, 2H, Ar).

MS, (+)FAB, m/e 415(M+H), m/e 437(M+Na).

Anal. Calc. for C, 55.07; H, 5.11; N, 6.76 Anal. found for C, 54.94; H, 5.22; N, 6.76

Conjugation of (S)-N-[2-[4-[4-[(2,5-Dioxo-1-pyrrolidinyl)-oxy]-4 -oxobutyl]phenyl]-1-methyl-ethyl]-2-trifluoroacetamide (amphetamine) to Bovine Serum Albumin (BSA):

To a solution (400 mL) containing sodium bicarbonate (0.05M), 10% dimethylsulfoxide (DMSO), and BSA (6.0 g) at pH 8.0, 25° the N-hydroxysuccinimide ester (4) (0.035 g in 32.6 mL of DMSO) was added dropwise. The reaction was stirred at 4° for 15 h and dialyzed as in Example 4. After dialysis the protein concentration was measured and adjusted to 0.0005 g per mL.

EXAMPLE 8

Preparation of sensitized latex containing the amphetamine-BSA conjugate-general procedure.

To a stirred latex (Seradyn carboxy modified polystyrene 0.888 microns) suspension (180 mL, 10% solids), N-hydroxybenzotriazole (NHB) (0.6 g in 24 mL of aqueous dimethylformamide) and 1-cyclohexyl-3-(2-morpholinoethyl) carbodiimide metho p=toluenesulfonate (CMC) (2.0 g in 32 mL of water) were added. The suspension was stirred for 3 h at 4° then diluted to 2% latex and extensively washed with water by tangential flow filtration. To the washed 2% latex were added 900 mL of the amphetamine-BSA solution from Example 7. The reaction was stirred overnight at 4° and was again extensively washed with water by tangential flow filtration. The washed latex was then taken off the filtration apparatus and pelleted by centrifugation. The pellets were resuspended in 3000 mL of sodium carbonate (pH 11.4, 0.10M) and allowed to stir at room temperature for 24 h. The mixture was again pelleted by centrifugation, resuspended in 2000 mL of phosphate buffer (pH 6, 0.05M), put back on the tangential flow filtration system and extensively washed with water. The washed latex was then adjusted to 3.0% latex solids (by weight) concentration.

EXAMPLE 9

Amphetamine Test

Preparation of reaction buffer for test:

This diluent consists of the following in aqueous solution at pH 7.5:

1. Pipes [0.20M, 1,4-piperazine bis(ethanesulfonic acid)]
2. PVP [0.80%, Polyvinylpolypyrrolidone]
3. PEG 8000 [1.50%, Poly(ethylene glycol)]
4. Sodium Chloride [20%]
5. Sodium Azide [0.1%]

Preparation of antiserum buffer for test:

Sheep antiserum against amphetamines is diluted in an appropriate buffer system. This diluent consists of the following in aqueous solution at pH 7.2:

1. Hepes, [0.05M, 4- (2-hydroxyethyl)-piperazine-ethanesulfonic acid]
2. BSA (0.25%)
3. Sodium Chloride (0.15%)
4. Sodium Azide (0.15%)

Test Methodology

Ten microliters of amphetamine free urine is dispensed into a mixing well of a capillary agglutinography slide followed by 50 microliters each of antiserum buffer, reaction buffer and latex (example 8). The added liquids are stirred for three seconds and the solution is moved to allow contact with the capillary. The liquid will move through the capillary and fill the viewing area at the end of the capillary in three to six minutes. The liquid in the viewing area will appear as fine floccules (agglutinated) or milky. For negative samples agglutination should be very strong with very little cloudiness.

The dilution of a particular antiserum which is chosen for the test is the one which has the highest dilution that will still produce strong agglutination in the viewing area. When various amounts of amphetamine are dissolved in amphetamine free urine in the test systems, no agglutination occurs. The amount of amphetamine required to inhibit the agglutination will vary from 250 nanograms per mL or greater depending on the concentration of antiserum used and the strength of antiserum produced. Thus, for the system described above a urine containing 1000 nanograms of amphetamine per mL is sufficient to partially inhibit agglutination and a urine containing 1500 nanograms of amphetamines per mL is sufficient to completely inhibit agglutination.

The following table reports the type of cross-reactivity that is observed in the system described above:

|  | Concentration (ng/mL) equivalent to 300 ng/mL of Morphine | % Cross reactivity |
| --- | --- | --- |
| p-Hydroxyamphetamine | 5,000 | 20 |
| Tyramine HCl | 100,000 | 0.01 |

The following table reports the type of specificity and accuracy that is observed with the above described assay when used with samples positive for amphetamine:

|  |  | Gas Chromatography-Mass Spectroscopy | |
| --- | --- | --- | --- |
|  |  | + | |
| Agglutination | + | 45 | |
| Test | − | 1* | |

*The one discrepant sample was shown to contain drug at a concentration close to the cut-off (1,000 ng/mL) of the assay.

EXAMPLE 10

Preparation of tetrahydrocannabinoid reagent

Preparation of 1-[[(6a, 7, 10, 10a-Tetrahydro-1-hydroxy-6,6-dimethyl-3-pentyl-6H-dibenzo[b,d]pyran-1-yl(carbonyl]oxy]-2,5-pyrrolidinedione:

To a solution of 1.26 g (3.67 m mole) of 11-nor-Δ$^8$-THC-9-carboxylic acid[1] in 50 mL of 1:1 ethylacetate/methylene chloride were added 1.68 g (14.7 mmole) of N-hydroxysuccinimide and 2.10 g (11.0 mmole) of 1-(3-dimethylaminopropyl)3-ethylcarbodiimide hydrochloride. The reaction was stirred for 16 hours at room temperature. The reaction mixture was washed with 1N hydrochloric acid (3×100 mL), water (3×100 mL) and saturated brine (100 mL). The organic phase was dried over Na$_2$SO$_4$ and concentrated under reduced pressure. Chromatography over silica gel (Flash, 2 inches×6 inches). Eluting with 40% ethylacetate in hexane afforded 1.41 g (87%) of the desired N-hydroxysuccinimide ester. Satisfactory NMR, IR and MS were obtained.

IR(KBr) 3415(OH), 1802, 1760, 1738 (c=0) cm$^{-1}$, $^1$H NMR (CDCl$_3$)δ0.88(t, J=6 Hz, 3H, CH$_3$), 1.13(s, 3H, CH$_3$), 1.40 (s, 3H, CH$_3$), 2.86(bs, 4H, CH$_2$), 6.11(s, 1H, Ar), 6.27 (s, 1H, Ar), 7.32(d, J=4 Hz, 1H, vinyl). MS, m/e 441(M+)

Conjugation of 1-[[(6a, 7, 10, 10a-Tetrahydro-1-hydroxy-6,6-dimethyl-3-pentyl-6H-dibenzo)oxy][b,d]pyran-1-yl-(carbonyl]oxy]-2,5-pyrrolidinedione (cannabinoid) to Bovine Serum Albumin (BSA):

To a solution (300 mL) containing sodium bicarbonate (0.05M), 10% dimethylsulfoxide (DMSO), and BSA (4.5 g) at pH 8.5, 25° the N-hydroxysuccinimide ester (0.006 g in 6.2 mL of DMSO) was added dropwise. The reaction was stirred at 4° for 15 h and dialyzed as in Example 4. After dialysis the protein concentration was measured and adjusted to 0.005 g per mL.

EXAMPLE 11

Preparation of sensitized latex containing the cannabinoid-BSA conjugate—general procedure.

To a stirred latex (Seradyn carboxy modified polystyrene 0.888 microns) suspension (180 mL, 10% solids), N-hydroxybenzotriazole (NHB) (0.6 g in 24 mL of aqueous dimethylformamide) and 1-cyclohexyl-3-(2-morpholinoethyl)carbodiimide metho p-toluenesulfonate (CMC) (2.0 g in 32 mL of water) were added. The suspension was stirred for 3 h at 4° then diluted to 2% latex and extensively washed with water by tangential flow filtration. To the washed 2% latex were added 900 mL of the opiate-BSA solution from Example 10. The reaction was stirred overnight at 4° and was again extensively washed with water by tangential flow filtration. The washed latex was then adjusted to a 2.2% latex solids (by weight) concentration.

EXAMPLE 12

THC Test

Preparation of reaction buffer for test:

This diluent consists of the following aqueous solution at pH 6.5:

1. Hepes [0.05M, 4-(2-hydroxyethyl)-1-piperazineethanesulfonic acid]
2. PVP [0.50%, Polyvinylpolypyrrolidone]
3. PEG 8000 [1.00%, Poly(ethylene glycol)]
4. Sodium Chloride [0.5%]
5. Sodium Azide [0.1%]

Preparation of antiserum buffer for test:

Purified mouse monoclonal antibody against cannabinoids is diluted in an appropriate buffer system. This diluent consists of the following in aqueous solution in pH 7.0:

1. Hepes (0.05M)
2. BSA (0.25%)
3. Sodium Chloride (0.15%)
4. Sodium Azide (0.15%)

Test Methodology:

Ten microliters of cannabinoid free urine is dispensed into a mixing well of a capillary agglutinography slide followed by 50 microliters each of antiserum buffer, reaction buffer and latex reagent (example 11). The added liquids are stirred for three seconds and the solution is moved to allow contact with the capillary. The liquid will move through the capillary and fill the viewing area at the end of the capillary in three to six minutes. The liquid in the viewing area will appear as fine floccules (agglutinated) or milky. For negative samples agglutination should be very strong with very little cloudiness.

The dilution of a particular antiserum which is chosen for the test is the one which has the highest dilution that will still produce strong agglutination in the viewing area. When various amounts of cannabinoids are dissolved in cannabinoid free urine in the test systems, no agglutination occurs. The amount of cannabinoid required to inhibit the agglutination will vary from 50 nanograms per mL or greater depending on the concentration of antiserum used and the strength of antiserum produced. Thus, for the system described above a urine containing 100 nanograms of cannabinoid per mL is sufficient to partially inhibit agglutination and a urine containing 600 nanograms of cannabinoid per mL is sufficient to completely inhibit agglutination.

The following table reports the type of cross-reactivity that is observed in the system described above:

|  | Concentration (ng/mL) equivalent to 300 ng/mL of Δ$^8$THC | % Cross reactivity |
| --- | --- | --- |
| 11-Hydroxy-cannabinol | 2,000 | 5.0 |
| Cannabinol | 800 | 12.5 |
| Δ$^9$-THC | 10,000 | 1.0 |
| 11-Hydroxy-Δ$^9$-THC | 2,000 | 5.0 |
| 8β-11-Dihydroxy-Δ$^9$-THC | 4,000 | 2.5 |
| 8β-Hydroxy-Δ$^9$-THC | 4,000 | 2.5 |

The following table reports the type of specificity and accuracy that is observed with the above described assay when used with samples positive for cannabinoids:

|  | Gas Chromatography-Mass Spectroscopy | |
| --- | --- | --- |
|  | + | — |
| Agglutination Test + | 43 | |
| Agglutination Test − | | 2* |

*The two discrepant samples were shown to contain drug near the cut-off (100 ng/mL) of the assay.

We claim:

1. A composition of the formula

P—[A—D]$_n$ where

D is a drug derivative antigenically selective for the determination of the presence of target drug or target drug metabolite, A is an activating linker-spacer group having an N-hydroxysuccinimide or isothiocyanate derived linking moiety,

P is a poly(amino acid) covalently bonded to A, and n is less than 1.

2. The composition of claim 1 wherein A—D is an activated drug derivative selected from the group consisting of a Δ$^8$THC derivative with A as a substituent at the 9-carbon thereof, a 5-substituted barbituric acid derivative with A as a second substituent at the 5-carbon thereof, a phencyclidine derivative with A as a substituent on the benzene thereof, a morphine derivative with A as a substituent on the 3-hydroxyl thereof, a benzoyl ecgonine derivative with A as a substituent on the benzene thereof, a 1,4 benzodiazepine derivative with A as a substituent on the 1 nitrogen thereof, and an amphetamine derivative with A as a substituent on the benzene thereof.

3. The composition of claim 1 wherein —[A–D] is the thiourea bound residue of an isothiocyanate activated derivative of the formula:

and the isothiocyanate is met or para.

4. The composition of claim 1 wherein —[A–D] is the thiourea bound residue of an isothiocyanate activated derivative of the formula:

where $R_1$ is hydrogen, methyl or acetyl, a is 2 to 8, and the isothiocyanate is meta or para.

5. The composition of claim 1 wherein —[A–D] is the amide bound residue of a hydroxysuccinimide activated derivative of the formula:

where $R^2$ is hydrogen or methyl, b is 1 to 9, and the alkylene group is bound to the benzene ring in the meta or para position.

6. The composition of claim 1 wherein —[A–D] is the amide bound residue of a hydroxysuccinimide activated derivative of the formula:

and $R^3$ is hydrogen or methyl.

7. The composition of claim 1 wherein —[A–D] is the thiourea bound residue of an isothiocyanate activated derivative selected from the group consisting of:
  N-[3-[7,8-Didehydro-4,5-epoxy-6-hydroxy-17-methyl-morphinan-3-yl)oxy]propoxy]-4-isothiocyanatobenzamide,
  N-[1-(4-Isothiocyanophenyl)ethyl]-4-[1-(1-piperidinyl)-1-cyclohexyl]benzamide, and
  N-[2-[7-Chloro-5-(2-fluorophenyl)-2,3-dihydro-2-oxo-1H-1,4-benzodiazepin-1-yl]ethyl]-4-isothiocyanatobenzamide.

8. The composition of claim 1 wherein —[A–D] is the amide bound residue of the hydroxysuccinimide activated derivative selected from the group consisting of:
  5-[3-[2,5-Dioxo-1-pyrrolidinyl)oxy]-1-methyl-3-oxopropyl]-5-(2-propenyl)2,4,6-1H,3H,5H)pyrimidimetrione,
  (S)-N[2-[4-[4-[(2,5-Dioxo-1-pyrrolidinyl)-oxy]-4-oxobutyl]phenyl]-1-methyl-ethyl]-2-trifluoroacetamide,
  (S)-N-Methyl-N[2-[4-[4-[(2,5-Dioxo-1-pyrrolidinyl)oxy]-4-oxo-butyl]-1-methyl-ethyl]-2-trifluoroacetamide,
  [1R-(exo,exo,anti)]-8-Methyl-3-[[4-[[[[[[(2,5-dioxo-pyrolidin-1-yl)oxy]carbonyl]phenyl]amino](thioxomethyl)]amino]methyl]benzoyl]oxy]bicyclo[3,2,1 ]octane-2-carboxylic acid,
  1[4-[1-(1-Piperidinyl)-1-cyclohexyl]benzoyloxy]-2,5-pyrrolidinedione, and
  1-[[(6a,7,10,10a-Tetrahydro-1-hydroxy-6,6-dimethyl-3-pentyl-6H-dibenzo)oxy][b,d]pyran-1-yl(carbonyl]oxy]-2,5-pyrrolidinedione.

9. The composition of any of claims 1, 2 or 3–8 wherein P is further bound to microparticles.

10. The composition of any of claims 1, 2 or 3–8 wherein n is below 0.5

11. The composition of claim 9 wherein n is below 0.5

12. The microparticular composition of claim 9, wherein P is covalently bound to latex microparticles.

13. The composition of claim 12, wherein P is bovine serum albumin.

* * * * *